United States Patent
Ito

(10) Patent No.: US 7,722,764 B2
(45) Date of Patent: May 25, 2010

(54) GRADIENT PUMP APPARATUS

(75) Inventor: Shinya Ito, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 884 days.

(21) Appl. No.: 11/584,564

(22) Filed: Oct. 23, 2006

(65) Prior Publication Data

US 2007/0034557 A1  Feb. 15, 2007

Related U.S. Application Data

(62) Division of application No. 10/981,493, filed on Nov. 5, 2004, now Pat. No. 7,141,161.

(30) Foreign Application Priority Data

Nov. 7, 2003  (JP) ............................. 2003-378054

(51) Int. Cl.
*B01D 15/08* (2006.01)
(52) U.S. Cl. .................... 210/198.2; 210/101; 210/143; 210/656; 417/2
(58) Field of Classification Search ................. 210/635, 210/656, 659, 101, 137, 143, 416.1; 417/3, 417/4, 5, 6, 7, 8
See application file for complete search history.

(56) References Cited

U.S. PATENT DOCUMENTS 5,393,434 A  2/1995  Hutchins et al.

(Continued)

FOREIGN PATENT DOCUMENTS

CA  2445939  12/2002

(Continued)

OTHER PUBLICATIONS

PTO Translation 2006-3696 of Japan Patent No. 2002-71657 Apr. 2006.*

(Continued)

*Primary Examiner*—Ernest G Therkorn
(74) *Attorney, Agent, or Firm*—Dickstein Shapiro LLP

(57) ABSTRACT

A gradient pump apparatus which is capable of continuously and precisely feeding, to a chromatograph, eluents at intervals of certain time and at a constant flow rate in units of nano-liter per minute while the composition of two or more eluent components is changed. The gradient pump apparatus includes a 10-port valve for switching an eluent mixing pipe, in which a feed pressure of eluents changes with time, to be connected to a first loop which is supplied with another eluent from an isocratic pump that should function to hold an eluent feed pressure constant, and which is connected to an analytic section, or to a second loop through which the eluents are drained. A controller computes a difference between a value of the pressure in the eluent mixing pipe and a value of the eluent feed pressure applied from the isocratic pump when the eluent mixing pipe is connected to the second loop. At the time when the eluent mixing pipe is connected to the first loop with shift of the 10-port valve, the feed speed of the isocratic pump is determined based on the above pressure difference. The isocratic pump is controlled in sync with the valve shift so that the determined feed speed of the isocratic pump is obtained.

4 Claims, 4 Drawing Sheets

U.S. PATENT DOCUMENTS

2005/0016263 A1  1/2005  Yamauchi et al.
2006/0000759 A1  1/2006  Takao et al.

FOREIGN PATENT DOCUMENTS

| JP | 2002-71657 | 3/2002 |
| JP | 2002-365272 | 12/2002 |
| JP | 2003-98166 | 4/2003 |

OTHER PUBLICATIONS

PTO Translation 2006-3692 of Japan Patent No. 2003-98166a.*

* cited by examiner

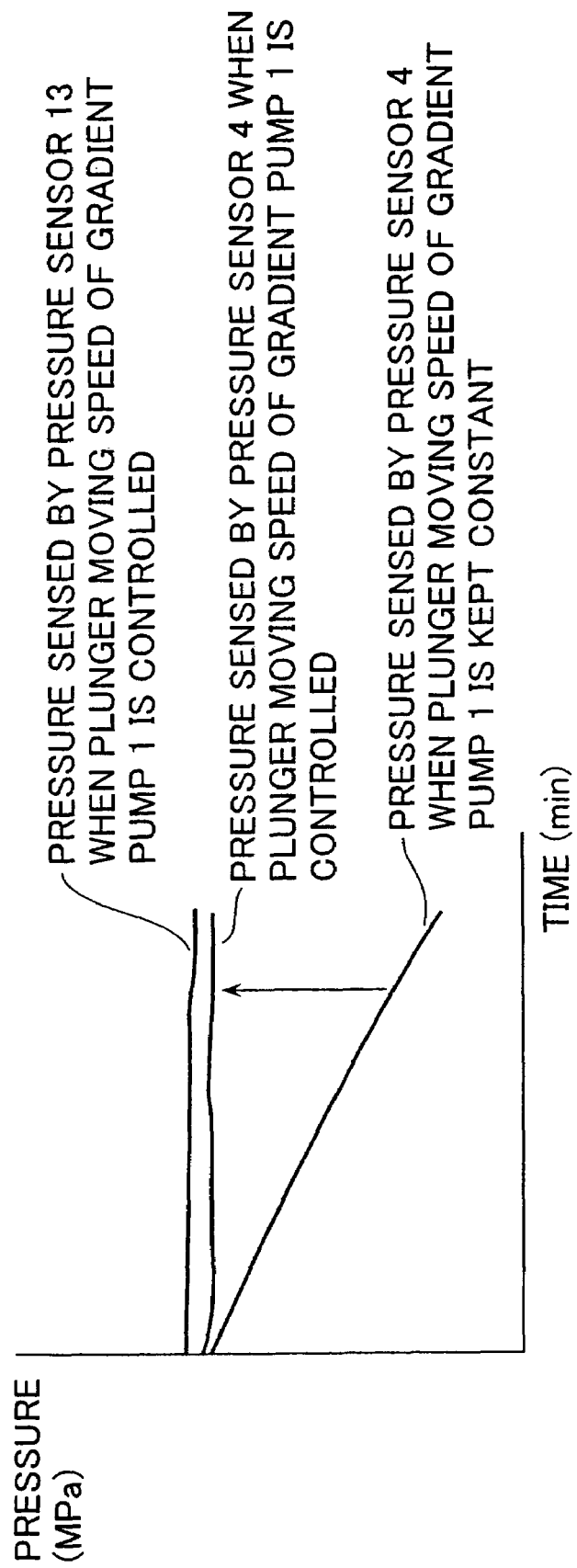

GRADIENT PUMP APPARATUS

CROSS-REFERENCE TO RELATED APPLICATION

This application is a division application of U.S. patent application Ser. No. 10/981,493, filed on Nov. 5, 2004, now U.S. Pat. No. 7,141,161 the disclosure of which is incorporated in its entirety by reference herein.

BACKGROUND OF THE INVENTION

1. Field of the Invention

The present invention relates to chromatographic technology, and more particularly to a gradient pump apparatus used for performing chromatography at a flow rate area of nano-liter per minute ($10^{-9}$ L/min), and a chromatograph using the gradient pump apparatus.

2. Description of the Related Art

Several techniques have hitherto been proposed for chromatographs in which chromatography of a mixture is performed through gradient elution at a flow rate in units of nano-liter per minute.

According to techniques disclosed in a Patent References 1 JP,A 2002-71657 and a Patent Reference 2 JP,A 2002-365272, for example, plural types of gradient solutions required for one analysis item are filled in one or plural flow passages beforehand, and those solutions are successively fed by a pump capable of feeding a solution at a constant flow rate.

Also, a Patent reference 3 JP,A 2003-98166 discloses another technique. According to this technique, at least two feeder units are communicated with each other, and the pressure of a solution fed from a first feeder unit is sensed by a pressure sensor so that the solution is delivered at a desired setting value. Then, a second feeder unit pre-pressurizes the solution corresponding to the delivery pressure of the first feeder unit. In other words, this technique is intended to feed the solution with high accuracy free from disturbances in the solution feed.

According to still another known technique, a gradient solution is fed by a pump capable of feeding the solution at a flow rate in units of micro-liter per minute ($10^{-6}$ L/min), and a splitter is disposed in a flow passage to split a part of the fed solution such that the solution can be fed at a flow rate in units of nano-liter per minute.

Still another known technique employs a plurality of pumps each utilizing an electroosmotic flow. Then, gradient feed is performed by feeding plural types of solutions with the respective pumps while directly mixing the solutions with each other.

SUMMARY OF THE INVENTION

In the chromatographs in which chromatography of a mixture is performed through gradient elution at a flow rate in units of nano-liter per minute, there is a demand for continuously and precisely performing the chromatography at intervals of certain time while the composition of two or more eluent components is changed. This is because the efficiency of analysis can be increased if it is possible to continuously and precisely perform the chromatography at intervals of certain time while the composition of two or more eluent components is changed.

The techniques disclosed in Patent References 1 and 2 are proposed to meet that demand as follows. Plural types of gradient solutions (eluents) are filled in one or plural first flow passages, and the first flow passages are connected through a valve to a second flow passage to which is connected a pump capable of feeding a solution at a constant flow rate. Then, the eluents are delivered to an analytic section at a constant flow rate while the valve is shifted at proper timing.

However, because the pressure in the first flow passage is usually higher than that in the second flow passage, the difference between the solution pressures causes compression of the solution residing in the second flow passages and generates a pressure variation at the time when the valve is shifted. This results in a difficulty in feeding the solution at an exactly constant flow rate in units of nano-liter per minute.

In the technique disclosed in Patent Reference 3 and other known techniques, a similar problem also occurs when employing the arrangement that a first flow passage for gradient feed is connected through a valve to a second flow passage for feed at a constant flow rate. Thus, as mentioned above, a pressure variation occurs at the time when the valve is shifted, and hence a difficulty arises in feeding the solution at an exactly constant flow rate in units of nano-liter per minute.

Accordingly, it is an object of the present invention to realize a gradient pump apparatus capable of continuously and precisely feeding, to a chromatograph, eluents at intervals of certain time and at a constant flow rate in units of nano-liter per minute while the composition of two or more eluent components is changed.

To achieve the above object, the present invention is constructed as follows:

(1) A gradient pump apparatus according to one aspect of the present invention comprises a gradient pump capable of mixing and feeding plural types of solutions at a flow rate in units of micro-liter per minute; an isocratic pump capable of feeding a solution at a flow rate in units of nano-liter per minute; a switching valve for switching the solutions fed from the gradient pump to be sent to an analytic section with the solution fed from the isocratic pump, or to be drained; a first pressure sensor for sensing a solution feed pressure of the gradient pump; a second pressure sensor for sensing a solution feed pressure of the isocratic pump; and an operation control unit.

The operation control unit computes a difference between the pressure sensed by the first pressure sensor and the pressure sensed by the second pressure sensor, extracts a solution feed pressure of the isocratic pump in accordance with the computed pressure difference, shifts the switching valve such that the solutions fed from the gradient pump are sent to the analytic section with the solution fed from the isocratic pump, and controls operation of the isocratic pump in match with shift timing of the switching valve such that the solution feed pressure of the isocratic pump is held at a value of the extracted solution feed pressure.

(2) A gradient pump apparatus according to another aspect of the present invention comprises a gradient pump capable of mixing and feeding plural types of solutions at a flow rate in units of micro-liter per minute; an isocratic pump capable of feeding a solution at a flow rate in units of nano-liter per minute; a switching valve for switching the solutions fed from the gradient pump to be sent to an analytic section with the solution fed from the isocratic pump, or to be drained; a first pressure sensor for sensing a solution feed pressure of the gradient pump; a second pressure sensor for sensing a solution feed pressure of the isocratic pump; and an operation control unit.

The operation control unit computes a difference between the pressure sensed by the first pressure sensor and the pressure sensed by the second pressure sensor, and controls operation of the gradient pump such that the computed pressure difference approaches zero.

(3) A gradient pump apparatus according to still another aspect of the present invention comprises a gradient pump capable of mixing and feeding plural types of solutions at a flow rate in units of micro-liter-per minute; an isocratic pump capable of feeding a solution at a flow rate in units of nano-liter per minute; a switching valve for switching the solutions fed from the gradient pump to be sent to an analytic section with the solution fed from the isocratic pump, or to be drained; a memory storing a difference between a value of a solution feed pressure of the gradient pump, which changes with the lapse of time, and a value of a solution feed pressure of the isocratic pump; and an operation control unit.

The operation control unit extracts a solution feed pressure of the isocratic pump in accordance with the pressure difference stored in the memory, and shifts the switching valve such that the solutions fed from the gradient pump are sent to the analytic section with the solution fed from the isocratic pump.

Further, the operation control unit controls operation of the isocratic pump in match with shift timing of the switching valve such that the solution feed pressure of the isocratic pump is held at a value of the extracted solution feed pressure.

(4) A liquid chromatograph according to the present invention comprises a sample injection device constituted by a gradient pump apparatus according to any one of above (1), (2), (3) and (4), a microbore column, and a detector for liquid chromatography.

Thus, the present invention can realize the gradient pump apparatus capable of continuously and precisely feeding, to a chromatograph, eluents at intervals of certain time and at a constant flow rate in units of nano-liter per minute while the composition of two or more eluent components is changed, and can also realize a liquid chromatograph using the gradient pump apparatus.

According to the gradient pump apparatus of the present invention, since the chromatography can be performed in a continuous and precise manner, the efficiency of analysis can be increased.

BRIEF DESCRIPTION OF THE DRAWINGS

FIG. 6 is a graph showing pressure variations in a flow passage in another embodiment of the present invention.

DESCRIPTION OF THE PREFERRED EMBODIMENTS

Embodiments of the present invention will be described below with reference to the attached drawings.

Figure 1:
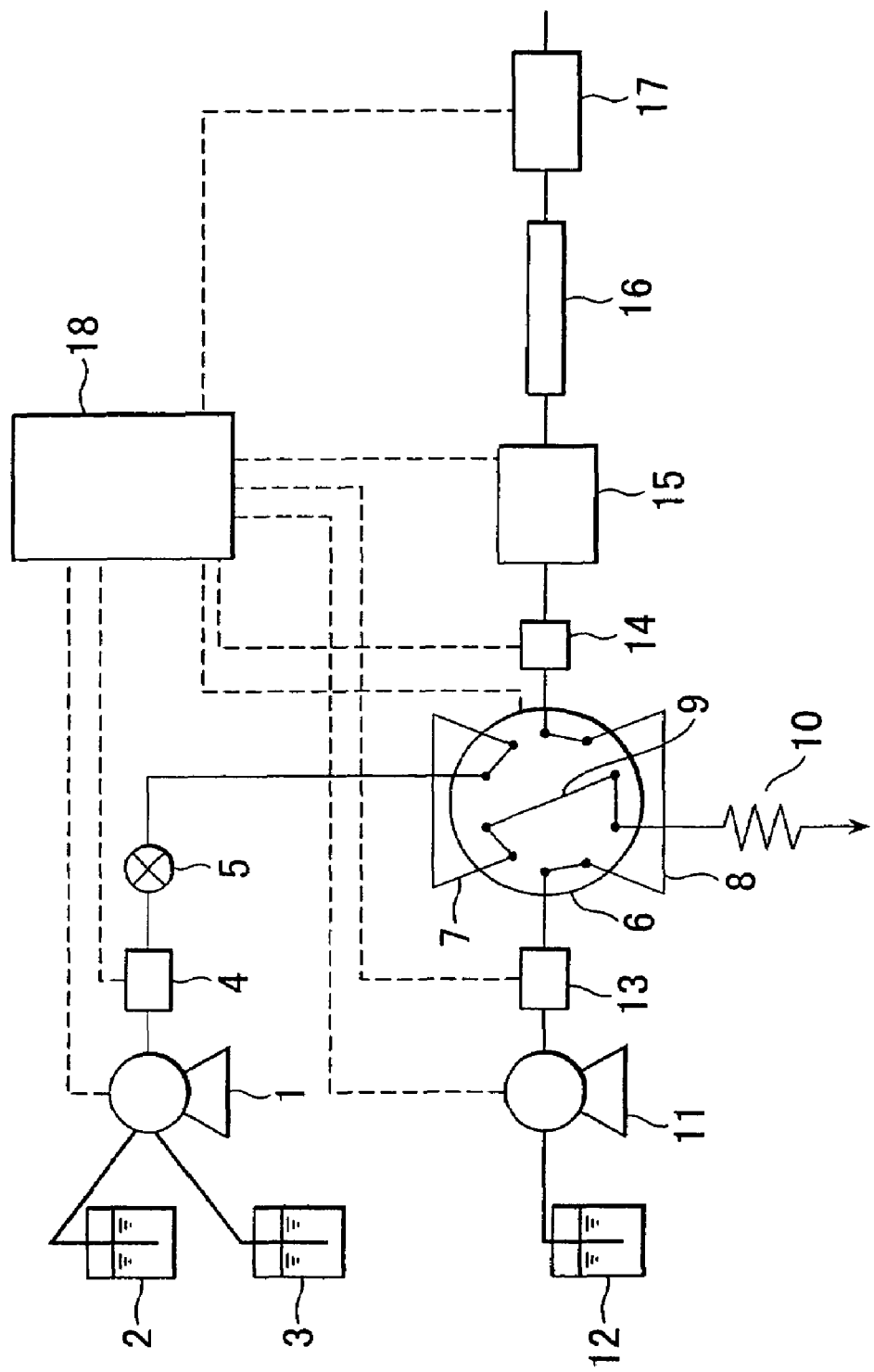
FIG. 1 is a block diagram of a liquid chromatograph using a gradient pump apparatus according to one embodiment of the present invention.

FIG. 1 is a block diagram of a liquid chromatograph using a gradient pump apparatus according to one embodiment of the present invention.

Referring to FIG. 1, two types of eluents 2, 3 are mixed and fed by a gradient pump 1 at a flow rate in units of micro-liter per minute while the composition of those eluents is changed. After passing a pressure sensor 4, the eluents fed from the gradient pump 1 are sufficiently mixed by a mixer 5 and are sent as a gradient solution to a 10-port valve 6.

The 10-port valve 6 is provided with two gradient loops 7, 8. The gradient solution passes one of the gradient loops 7, 8 and is then discharged as a drain to the exterior through a bypass 9 and a resistance coil 10.

On the other hand, an eluent 12 is fed from an isocratic pump 11 at a flow rate in units of nano-liter per minute and is sent to the 10-port valve 6 after passing a pressure sensor 13, thereby pushing out the solution in the other of the gradient loops 7, 8 associated with the 10-port valve 6. By shifting flow passages in the 10-port valve 6 at intervals of a certain time, the gradient solution filled in either one of the gradient loops is sent to a flow passage, which is extended to a flowmeter 14 and a sample injector 15, at a flow rate set by the isocratic pump 11.

When the gradient pump 1 produces and feeds the gradient solution having a different composition with the lapse of time, the produced gradient solution is continuously sent to the sample injector 15, an analytical column 16, and an ultraviolet-visible detector 17. As a result, the liquid chromatograph capable of performing the chromatograph while continuously feeding the gradient solution is realized.

In the arrangement described above, the gradient pump 1 can be constructed of any gradient pump generally used in liquid chromatography. Further, the isocratic pump 11 feeding the eluent at a flow rate in units of nano-liter per minute can be constructed of, for example, a syringe pump. Alternatively, a pump utilizing an electroosmotic flow is also usable.

In the state shown in FIG. 1, the pressure acting in the flow passage within the gradient loop 7 is decided primarily depending on the inner diameter and length of the resistance coil 10, but that pressure is also affected by the composition of the gradient solution fed at that time.

Usually, water and an organic solvent, such as acetonitrile, are often employed as eluents in the liquid chromatography. In such a case, when the proportion of the organic solvent changes, the eluent feed pressure is also changed. Therefore, even when the resistance coil 10 is selected such that the pressure in the gradient loop is constant for the composition of the gradient solution at the start of the measurement, the pressure in the gradient loop changes during one measurement cycle.

For example, when the gradient solution is fed while changing the solution composition from 100% of water to 100% of acetonitrile, the pressure acting in the gradient loop (i.e., the gradient loop 7 in the state of FIG. 1) connected to the gradient pump 1 gradually lowers with the lapse of measurement time.

On the other hand, the isocratic pump 11 always feeds the same eluent 12 under a constant feed pressure. Hence, there occurs a difference between the pressure in the gradient loop (i.e., the gradient loop 8 in the state of FIG. 1) connected to the isocratic pump 11 and the eluent feed pressure applied from the isocratic pump 11.

For that reason, unless any action is taken, the pressure in the flow passage from the isocratic pump 11 would be lowered immediately after the 10-port valve 6 has been shifted. Because it takes a time for the once lowered pressure to restore to the set level with the feed at a flow rate in units of nano-liter per minute, precise isocratic feed cannot be ensured.

Figure 2:
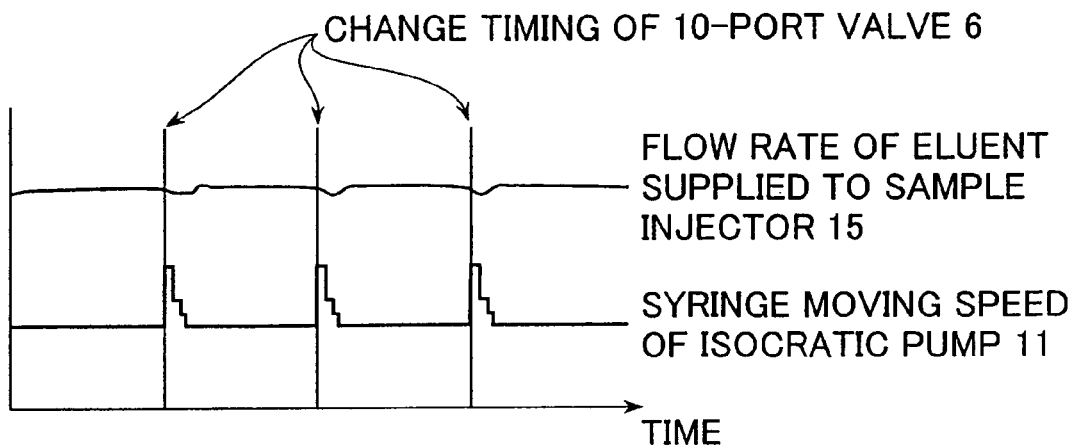
FIG. 2 is a graph showing variations over time in a syringe moving speed of an isocratic pump and an eluent flow rate in one embodiment of the present invention.

To avoid such a problem, this embodiment executes control as shown in FIG. 2. More specifically, the moving speed of a feed syringe of the isocratic pump 11 is increased in match with the shift-timing of the 10-port valve 6, thereby suppressing lowering of the pressure in the flow passage. As a result, a reduction of the flow rate is suppressed and the eluent feed at a constant flow rate can be realized.

The timing at which the moving speed of the feed syringe of the isocratic pump 11 is changed and the moving speed thereof after the change can be decided through the steps of monitoring pressure variations sensed by the pressure sensor 13, which is disposed in the flow passage, from a controller 18 and transmitting an optimum moving speed to the isocratic pump 11. As an alternative, the control can also be executed with the controller 18 through the steps of computing a difference between a pressure value sensed by the pressure sensor 4 and a pressure value sensed by the pressure sensor 13 before the shift of the 10-port valve 6, deciding the moving speed of the feed syringe of the isocratic pump 11 in accordance with the computed difference, and controlling the moving speed thereof in sync with the shift of the 10-port valve 6.

Thus, the controller 18 controls the moving speed of the feed syringe of the isocratic pump 11 (i.e., operates the isocratic pump 11 in accordance with a gradient program) so that the pressure value sensed by the pressure sensor 13 is held at a predetermined value.

The controller 18 has a memory incorporated in it. The memory stores the moving speed of the feed syringe of the isocratic pump 11 to be set at the shift of the 10-port valve 6 for each value of the pressure difference between the pressure sensors 4 and 13. The syringe moving speed stored in the memory is provided as a value that has been previously determined based on an experiment, etc.

When the pressure in the flow passage lowers upon the shift of the 10-port valve 6, a large fall of the pressure is caused immediately after the valve shift. In view of such a tendency, the syringe moving speed is controlled such that it is increased to a large extent immediately after the valve shift and then returned to the original speed in several stages while monitoring the pressure sensed by the pressure sensor 13. Such control is intended to suppress the pressure in the flow passage, i.e., the flow rate, from exceeding a setting value (namely, to prevent the so-called overshoot).

While the syringe moving speed is changed step by step in the example shown in FIG. 2, a similar advantage can also be obtained in the case of continuously changing the syringe moving speed along a curve.

Figure 3:
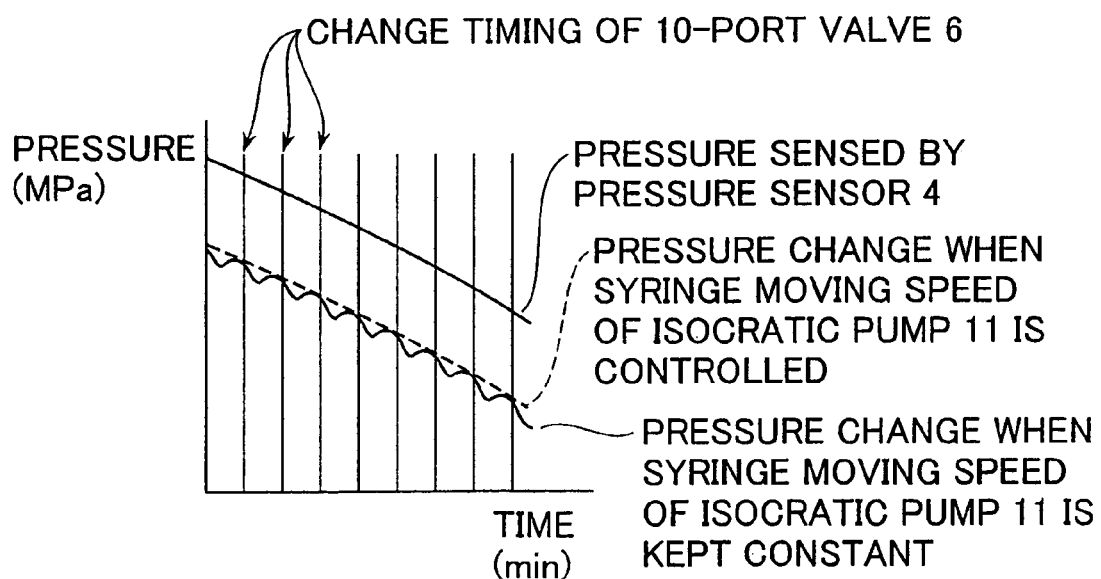
FIG. 3 is a graph showing pressure variations in a flow passage in one embodiment of the present invention.

FIG. 3 is a graph showing pressure variations in the flow passage when the syringe moving speed is held constant and when the syringe moving speed is changed in sync with the shift of the 10-port valve 6.

In FIG. 3, the pressure value sensed by the pressure sensor 4 lowers with the lapse of measurement time. Also, the syringe moving speed is controlled such that the pressure value sensed by the pressure sensor 13 also lowers in a linear pattern similarly to the pressure value sensed by the pressure sensor 4. Note that the pressure value sensed by the pressure sensor 4 is shown in FIG. 3 as being moved upward for the sake of easier understanding, but the actual pressure value is almost equal to the pressure value sensed by the pressure sensor 13.

As indicated by a broken line in FIG. 3, a variation time (amount) of the pressure value sensed by the pressure sensor 13 can be shortened (reduced) as a result of changing the syringe moving speed. Consequently, the gradient solution can be fed at a constant flow rate, as shown in FIG. 2, while maintaining the pressure in the flow passage at a constant level.

On the other hand, when the syringe moving speed is kept constant, a large pressure variation occurs at each shift timing of the 10-port valve 6.

Although a flow rate variation caused by a pressure shock generated upon the shift of the 10-port valve 6 cannot be completely eliminated, stability in solution feed can be maintained at a level enough for the liquid chromatography. Incidentally, a flow rate in units of nano-liter per minute can be measured by using a commercially available liquid mass flowmeter as the flowmeter 14.

Figure 4:
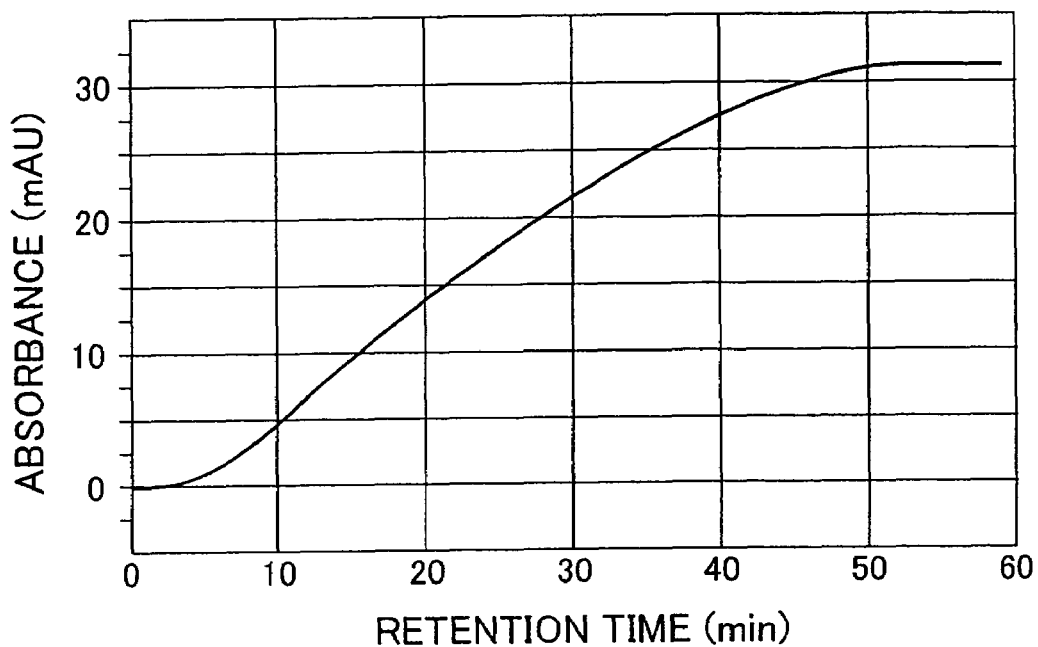
FIG. 4 is a graph showing measurement results of absorbance obtained with one embodiment of the present invention.

FIG. 4 is a graph showing measurement result data of absorbance obtained when a gradient solution was fed at a flow rate of 200 nano-liters per minute by using the gradient pump apparatus according to one embodiment of the present invention.

The data shown in FIG. 4 represents an eluent gradient curve measured by using the ultraviolet-visible detector 17 when water and acetonitrile containing 0.2% of acetone were fed at a flow rate of 50 micro-liters per minute from the gradient pump 1 and water was fed at a flow rate of 200 nano-liters per minute from the isocratic pump 11.

As seen from FIG. 4, a very smooth gradient curve is obtained when the gradient pump apparatus of the present invention is employed.

Figure 5:
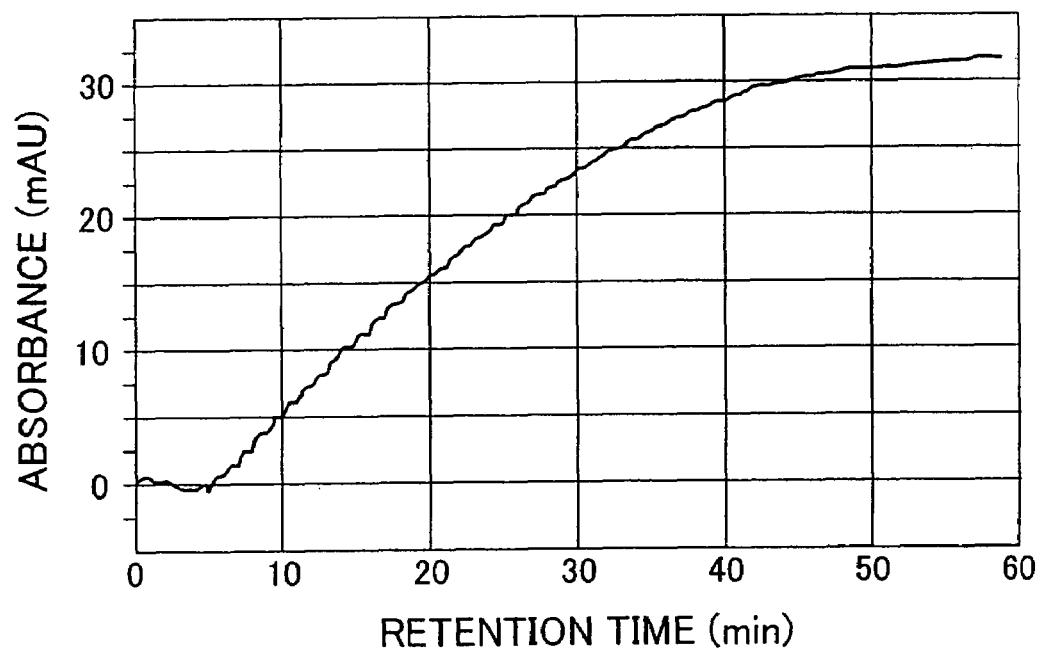
FIG. 5 is a graph showing measurement results of absorbance for comparison with the present invention.

FIG. 5 is a graph showing measurement result data of absorbance obtained when the syringe moving speed was not changed, for comparison with the present invention. In the case of not changing the syringe moving speed, because the eluent flow rate fluctuates with pressure variations caused during the gradient feed, there occur cyclic variations in the measured absorbance corresponding to the shift of the 10-port valve 6. It is thus understood that the precise gradient feed cannot be obtained.

As described above, this one embodiment of the present invention includes the 10-port valve for switching an eluent mixing pipe, in which the eluent feed pressure changes with the lapse of time, to be connected to a first loop which is supplied with another eluent from the isocratic pump that should function to hold the eluent feed pressure constant, and which is connected to the analytic section, or to a second loop through which the eluents are drained. Then, a difference between a value of the pressure in the eluent mixing pipe and a value of the eluent feed pressure applied from the isocratic pump is computed when the eluent mixing pipe is connected to the second loop.

Subsequently, at the time when the eluent mixing pipe is connected to the first loop with the shift of the 10-port valve 6, the feed speed of the isocratic pump is determined based on the above pressure difference immediately before the shift of the 10-port valve. The isocratic pump is controlled substantially in sync with the valve shift to operate at the determined feed speed.

Thus, in accordance with the sensed pressure value, the isocratic pump is controlled so that the first loop is held at the predetermined pressure.

Accordingly, a gradient pump apparatus can be realized which is capable of continuously and precisely feeding, to a chromatograph, an eluent at intervals of certain time and at a constant flow rate in units of nano-liter per minute while the composition of two or more eluent components is changed.

Also, a liquid chromatograph employing the gradient pump apparatus can be realized.

In another embodiment of the present invention, pressure variations in the flow passage caused due to the pressure difference between the gradient loops upon the shift of the 10-port valve 6 are suppressed by changing the plunger moving speed of the gradient pump 1, i.e., the flow rate in the gradient feed, instead of changing the eluent feed pressure of the isocratic pump 11.

This embodiment has the same entire system arrangement as that of the above-described embodiment shown in FIG. 1, but differs in the pump control method executed by the controller 18. In ordinary liquid chromatography, as in the above-described embodiment, water and an organic solvent are used as the two types of eluents 2, 3 and are fed by the gradient pump 1 while the composition of those eluents is changed during one measurement cycle.

Therefore, as the proportion of the organic solvent in the gradient solution changes, the eluent feed pressure is also changed, and the pressure difference between the two gradient loops varies during one measurement cycle. As a result, the gradient feed at a precise flow rate cannot be ensured.

To solve such a problem, the pressure sensed by the pressure sensor 13 in the flow passage extending from the isocratic pump 11 is always monitored by the controller 18, and is compared with the pressure sensed by the pressure sensor 4. Then, the plunger moving speed of the gradient pump 1 is changed so that the pressure difference between the two gradient loops 7 and 8 becomes zero.

For example, when water and acetonitrile are employed as the two types of eluents 2, 3 and the proportion of acetonitrile is gradually increased with the lapse of time, the pressure sensed by the pressure sensor 4 during the gradient feed gradually lowers with the lapse of time as indicated in FIG. 6 by a line representing "the pressure sensed by the pressure sensor 4 when the plunger moving speed is kept constant".

Such pressure lowering means that the pressures applied to the two gradient loops 7 and 8 are changed during one measurement cycle. Stated another way, because the pressure in the flow passage applied from the isocratic pump 11 is changed upon the shift of the 10-port valve 6, the precise eluent feed by the isocratic pump 11 cannot be ensured.

That problem is overcome by monitoring the pressure sensed by the pressure sensor 13 from the controller 18, and changing the plunger moving speed of the gradient pump 1 in a successive manner so that the pressure sensed by the pressure sensor 4 comes closer to the pressure sensed by the pressure sensor 13. With that control, the pressure sensed by the pressure sensor 4 is always held constant (as shown in FIG. 6) even when the condition of the eluent composition is changed.

As a result, the pressure difference between the two pressure sensors, i.e., the pressure difference between the two gradient loops, can be essentially eliminated during one measurement cycle, and hence the precise isocratic feed can be realized in spite of the shift of the 10-port valve 6.

In the embodiment shown in FIG. 1, the two pressure sensors 4 and 11 are provided. However, when the eluents used are restricted, the pressure varying with the lapse of time can be predicted in advance with no provision of the pressure sensors.

In such a case, the syringe moving speed can be controlled through the steps of storing pressure changes over time in a memory disposed within the controller 18 for each type and combination of eluents, computing the syringe moving speed corresponding to the pressure change, and adjusting the syringe moving speed in match with the shift timing of the 10-port valve 6.

Additionally, the analytical column 16 shown in FIG. 1 is a microbore column (e.g., a packed column, a monolithic column, or an open tube column). While the embodiment shown in FIG. 1 employs the ultraviolet-visible detector, a fluorescent detector or a detector utilizing atmospheric pressure ionization (e.g., an atmospheric pressure chemical ionization or an electrospray ionization) is also usable in place of the ultraviolet-visible detector.

What is claimed is:

1. A gradient pump apparatus comprising:
    a gradient pump capable of mixing and feeding plural types of solutions;
    an isocratic pump capable of feeding a solution;
    a switching valve for switching the solutions fed from said gradient pump to be sent to and analytic section with the solution fed from said isocratic pump, or to be drained;
    a first pressure sensor for sensing a solution feed pressure of said gradient pump;
    a second pressure sensor for sensing a solution feed pressure of said isocratic pump; and
    a control unit for computing a difference between the pressure sensed by said first pressure sensor and the pressure sensed by said second pressure sensor, extracting a solution feed pressure of said isocratic pump in accordance with the computed pressure difference, shifting said switching valve such that the solutions fed from said gradient pump are sent to said analytic section with the solution fed from said isocratic pump, and controlling operation of said isocratic pump in match with shift timing of said switching valve such that the solution feed pressure of said isocratic pump approaches at a value of said extracted solution feed pressure.

2. A gradient pump apparatus according to claim 1, wherein said gradient pump is a pump capable of mixing and feeding plural types of solutions at flow rate in units of microliter per minute.

3. A gradient pump apparatus according to claim 1, wherein said isocratic pump is a pump capable of feeding a solution at flow rate in units of nano-liter per minute.

4. A gradient pump apparatus according to claim 1, wherein said gradient pump or said isocratic pump controls to restrict the so-called overshoot.

* * * * *